United States Patent [19]

Schaefer

[11] Patent Number: 4,729,366

[45] Date of Patent: Mar. 8, 1988

[54] IMPLANTABLE HEARING AID AND METHOD OF IMPROVING HEARING

[75] Inventor: Donald W. Schaefer, Belleville, Wis.

[73] Assignee: Medical Devices Group, Inc., Madison, Wis.

[21] Appl. No.: 895,156

[22] Filed: Aug. 11, 1986

Related U.S. Application Data

[63] Continuation-in-part of Ser. No. 677,638, Dec. 4, 1984, abandoned.

[51] Int. Cl.$^4$ .............................................. H04R 25/00
[52] U.S. Cl. ..................................... 128/1.6; 128/420.6
[58] Field of Search ................... 128/419 R, 421, 784, 128/787, 1.6, 1 R, 420.5, 420.6; 381/68.3

[56] References Cited

U.S. PATENT DOCUMENTS

| | | | |
|---|---|---|---|
| 3,170,046 | 2/1965 | Leale | 179/107 |
| 3,346,704 | 10/1967 | Mahoney | 179/107 |
| 3,557,775 | 1/1971 | Mahoney | 128/1 |
| 3,712,962 | 1/1973 | Epley | 179/107 R |
| 3,764,748 | 10/1973 | Branch et al. | 179/107 E |
| 3,870,832 | 3/1975 | Fredrickson | 179/107 E |
| 3,882,285 | 5/1975 | Nunley | 179/107 E |
| 4,150,262 | 4/1979 | Ono | 179/107 BC |
| 4,284,856 | 8/1981 | Hockmaier et al. | 179/107 E |
| 4,357,497 | 11/1982 | Hockmaier et al. | 179/107 E |

OTHER PUBLICATIONS

G. J. Jako—Biomedical Engineering in Ear Surgery, Otolaryngologic Clinics of North America, vol. 5, No. 1, Feb. 1972.

Jako et al., Conservative Tympanoplasty, American Academy of Opthalmology and Otolarnology, Course 319, presented Oct. 1, 1966.

T. Ohno—The Implantable Hearing Aid (Part I) Audecibel, Fall 1984.

Aritomo et al., Audiological Assessment of Vibratory Hearing presented at 17th International Congress of Audiology meeting, Santa Barbara, Calif., Aug. 1984.

*Primary Examiner*—Edward M. Coven
*Attorney, Agent, or Firm*—Foley & Lardner

[57] ABSTRACT

A method and apparatus are disclosed for improving the hearing of a hearing-impaired subject who, if anatomically normal, possesses a tympanic membrane intended for generating mechanical tympanic vibration in response to sound waves impinging thereon, an inner ear responsive to mechanical vibrations, and an ossicular chain intended to communicate mechanical vibrations from the tympanic membrane to the inner ear; wherein the ossicular chain is interrupted to preclude transmission of mechanical vibrations between the tympanic membrane and the inner ear of the subject and an implant is surgically interposed to bridge the interruption in the ossicular chain to form an independent link between the tympanic membrane and the ear, which implant is comprised of input and output transducers for mediating mechanical/electrical signals to constitute that independent link.

52 Claims, 7 Drawing Figures

IMPLANTABLE HEARING AID AND METHOD OF IMPROVING HEARING

CROSS REFERENCE TO RELATED APPLICATION

This application is a continuation-in-part of application Ser. No. 677,638 filed Dec. 4, 1984, abandoned.

BACKGROUND OF THE INVENTION

The present invention relates to a device for improving the impaired hearing of a human subject, and more particularly, to a totally implantable hearing aid device.

In an anatomically normal human hearing apparatus, sound waves, which represent acoustical energy, are directed into an ear canal by the outer ear (pinna) and impinge upon a tympanic membrane (eardrum) interposed, at the terminus of the ear canal, between it and the middle ear space. The pressure of the sound waves effect tympanic vibrations in the eardrum, which then become manifested as mechanical energy. The mechanical energy in the form of tympanic vibrations is communicated to the inner ear by a sequence of articulating bones located in the middle ear space, which are generally referred to as the ossicular chain. The ossicular chain must be intact if acoustical energy existing at the eardrum is to be conducted as mechanical energy to the inner ear.

The ossicular chain includes three primary components, the malleus, the incus and the stapes. The malleus includes respective manubrium, neck and head portions. The manubrium of the malleus attaches to the tympanic membrane at a point known as the umbo. The head of the malleus, connected to the manubrium by the neck portion, articulates with one end of the incus, which provides a transmission path for the mechanical energy of induced vibrations from the malleus to the stapes. The stapes includes a capitulum portion connected to a footplate portion by means of a support crus and is disposed in and against a membrane-covered opening to the inner ear referred to as the oval window. The incus articulates with the capitulum of the stapes to complete the mechanical transmission path.

Normally, tympanic vibrations are mechanically conducted through the malleus, incus and stapes, to the oval window and therethrough to the inner ear (cochlea). These mechanical vibrations generate fluidic motion (transmitted as hydraulic energy) within the cochlea. Pressures generated in the cochlea by fluidic motion are accommodated by a second membrane-covered opening between the inner and middle ear, referred to as the round window. The cochlea translates the fluidic motion into neural impulses corresponding to sound perception as interpreted by the brain. However, various disorders of the tympanic membrane, ossicular chain and/or inner ear can occur to disrupt or impair normal hearing.

Various passive mechanical ossicular prosthesis and implantation techniques have been developed in connection with reconstructive surgery of the middle ear. See G. J. Jako, "Biomedical Engineering in Ear Surgery", *Otolaryngologic Clinics of North America*, Vol. 5, No. 1, Feb. 1972, and G. J. Jako, et al., "Conservative Tympanoplasty", American Academy of Opthalmology and Otolarynology, Course 319, presented Oct. 1, 1966.

Miniaturized electronic hearing aid devices which compensate for hearing disorders are also, in general, well known. Various of such devices are adapted to be entirely received within the ear canal or partly or completely implanted within the skull of a subject. Examples of such devices are those disclosed in U.S. Pat. No. 3,170,046, issued to L. P. Leale on Feb. 16, 1965; U.S. Pat. No. 3,712,962 issued to J. M. Epley on Jan. 23, 1973; U.S. Pat. No. 3,764,748 issued to J. P. Branch et al. on Oct. 9, 1973; U.S. Pat. Nos. 3,346,704 and 3,557,775 issued on Oct. 10, 1967 and Jan. 26, 1971, respectively to J. L. Mahoney; U.S. Pat. No. 3,870,832 issued to J. M. Fredrickson on Mar. 11, 1975; U.S. Pat. No. 4,150,262 issued to H. Ono on Apr. 17, 1979; and U.S. Pat. Nos. 4,284,856 and 4,357,497 both issued to I. J. Hochmaier et al. on Aug. 18, 1981 and Nov. 2, 1982, respectively. Further description of such devices is found in T. Ohno, "The Implantabale Hearing Aid" (Part I) Audecibel, Fall 1984 and Aritomo et al., "Audiological Assessment of Vibratory Hearing" presented at 17th International Congress of Audiology meeting, Santa Barbara, Calif., August 1984.

Perhaps the most interesting of the aforementioned U.S. patents is the '748 patent which implantable hearing aids including those which are configured for disposition principally within the middle ear space. The approach suggested there provides a transducer, which may be a piezoelectric crystal transducer, capable of converting mechanical vibrations within the ossicular chain into an output voltage. That output voltage may be applied to the area of the oval window to electrically stimulate it and may include a diode to rectify the variable voltage output of the transducer into a pulsating DC voltage to stimulate the auditory nerve. In another variant, the patentees suggest the incorporation of a piezoelectric crystal in the area of the oval window which receives the variable voltage signals from the transducer and vibrates to stimulate the auditory nerve. In any of these approaches, however, the proposed system also utilizes what the patentees regard as the natural distortion-free transmission of sound through the ossicular chain wherever possible. They say that, by virtue of leaving the ossicular chain intact, the acoustic energy impinging upon the eardrum passes through the ossicular chain in a distortion-free manner whereby the sound powered hearing aid they describe needs only supply minimal assistance to the hearing process. The description continues in the '748 patent to note that, as an alternative, the stapes may be removed and the hearing aid physically located in its stead where conditions permit. Under those circumstances, where the stapes is removed, the end of the incus is free-standing and the hearing aid is physically associated with it, such as by means of crimpable rings or the like. Thus the hearing aid serves as an integral part of the mechanical linkage in the transmission of forces from the eardrum to the oval window in all events, whether or not the integrity or continuity of the ossicular chain remains unimpaired. That being the case, mechanical feedback through the ossicular chain is a likely consequence, diminishing the overall efficacy of the approach suggested there.

Another example of an implantable hearing aid is described in U.S. Pat. No. 3,882,285 issued to J. A. Nunley et al. on May 6, 1975 and commonly assigned with the present invention. In accordance with the Nunley et al. invention, a self-contained miniature hearing device is implanted in the skull just behind the ear (pinna). The device includes a transducer, such as a microphone, a microphone port, an amplifier and a transmitter for providing a mechanical response to the sound received by the microphone. The microphone port is positioned in the ear canal. The transmitter of the preferred exemplary embodiment of Nunley et al. utilizes a piezoelectric crystal connected to the ossicular chain, preferably to the stapes.

The prior art systems, however, admit of room for improvement in that these known devices tend to be susceptible to interference by extraneous sounds and/or distortion of the sound ultimately perceived by the subject. Moreover, certain prior art systems tend to either include external or permanent transcutaneous or percutaneous components. Those with external components are aesthetically displeasing and susceptible to extrinsic forces. Transcutaneous elements typically utilize induction coils that are susceptible to misalignment and, further, consume high levels of power. Percutaneous elements such as a wire or tube protruding through the skin are inherently susceptible to infection. Other prior art systems utilize air-induced microphones disposed to be responsive to soundwaves for generating an electrical signal from which the stimulus to the inner ear is ultimately derived. Air-induced microphones are disadvantageous in that the microphone is typically either disposed external to the skull or requires a percutaneous element such as a microphone port or connecting wire. Moreover, the frequency response of air-induced microphones tends not to provide sufficient frequency range for realistic fidelity, and such microphones typically do not provide constant frequency sensitivity across their frequency band.

In the aforementioned presentation, "Conservative Tympanoplasty" by Jako et al., it was proposed that a relatively large piezoelectric crystal pickup transducer be built into the place of the tympanic membrane and directly drive a smaller piezoelectric crystal output transducer placed in the oval window. See Jako et al., supra, at pages 53–54. However, the Jako et al. system has reportedly never been reduced to practice, and the practicability of the system was noted as questionable by the authors themselves (See p. 53).

SUMMARY OF THE INVENTION

The present invention provides a method and apparatus for improving the impaired hearing of a subject utilizing a totally implantable device, not requiring any percutaneous elements and manifesting a frequency response commensurate with that provided by normal hearing. In accordance with one aspect of the present invention, the mechanical vibrations effected by the tympanic membrane (eardrum) are converted into electrical signals which are thereafter amplified and converted into mechanical vibrations and communicated to the inner ear. Conversion of mechanical energy to electrical energy is achieved by means of an input transducer which is surgically implanted within the ossicular chain, followed by suitable amplification of those electrical signals to account for both the level of hearing impairment suffered by the subject and the electromechanical response of the implanted device, and then the signals are converted to mechanical energy (vibrations) once again by an output transducer, all to achieve the desired level of aural enhancement for the wearer. These transducers and the associated circuitry thus comprise means for mediating mechanical/electrical energy within the middle ear space. In all instances the ossicular chain of the subject is interrupted to preclude transmission of mechanical vibrations between the tympanic membrane and the inner ear, with the implanted device interposed within the chain to bridge the interruption therein and form an electromechanically independent link, free from feedback, between the membrane and the inner ear.

In a particularly preferred variant of the present invention, the implanted device includes an input transducer means operatively associated with or proximate the eardrum for receiving mechanical tympanic vibrations therefrom and converting them into electrical signals characteristic of the acoustic energy creating those vibrations. Those signals are applied to appropriate electronic circuitry to amplify and perhaps otherwise control or condition them as may be required or found desirable. An output transducer means is operatively associated with or proximate the inner ear, preferably at or about the oval window, but perhaps proximate the round window if desired, for receiving amplified electrical signals and converting them into mechanical vibrations replicating the tympanic vibrations representative of the initiating acoustic energy. Those mechanical vibrations are thence processed in the cochlea in precisely the same way as mechanical vibrations would normally have been processed were the ossicular chain functionally complete; the magnitude of the vibrational energy at that juncture being controlled by the degree of amplification built within the total implant device. The transducers may be of any convenient and efficient design, including piezoelectric film transducers, piezoelectric crystal force transducers, piezoelectric accelerometers, or electromagnetic transducers. Preferred are the piezoelectric transducers, and most preferred is a piezoelectric transducer in an accelerometer configuration.

BRIEF DESCRIPTION OF THE DRAWING

Preferred exemplary embodiments of the present invention will hereinafter be described in conjunction with the appended drawing wherein like designations denote like elements and.

DETAILED DESCRIPTION OF A PREFERRED EXEMPLARY EMBODIMENT

Figure 1:
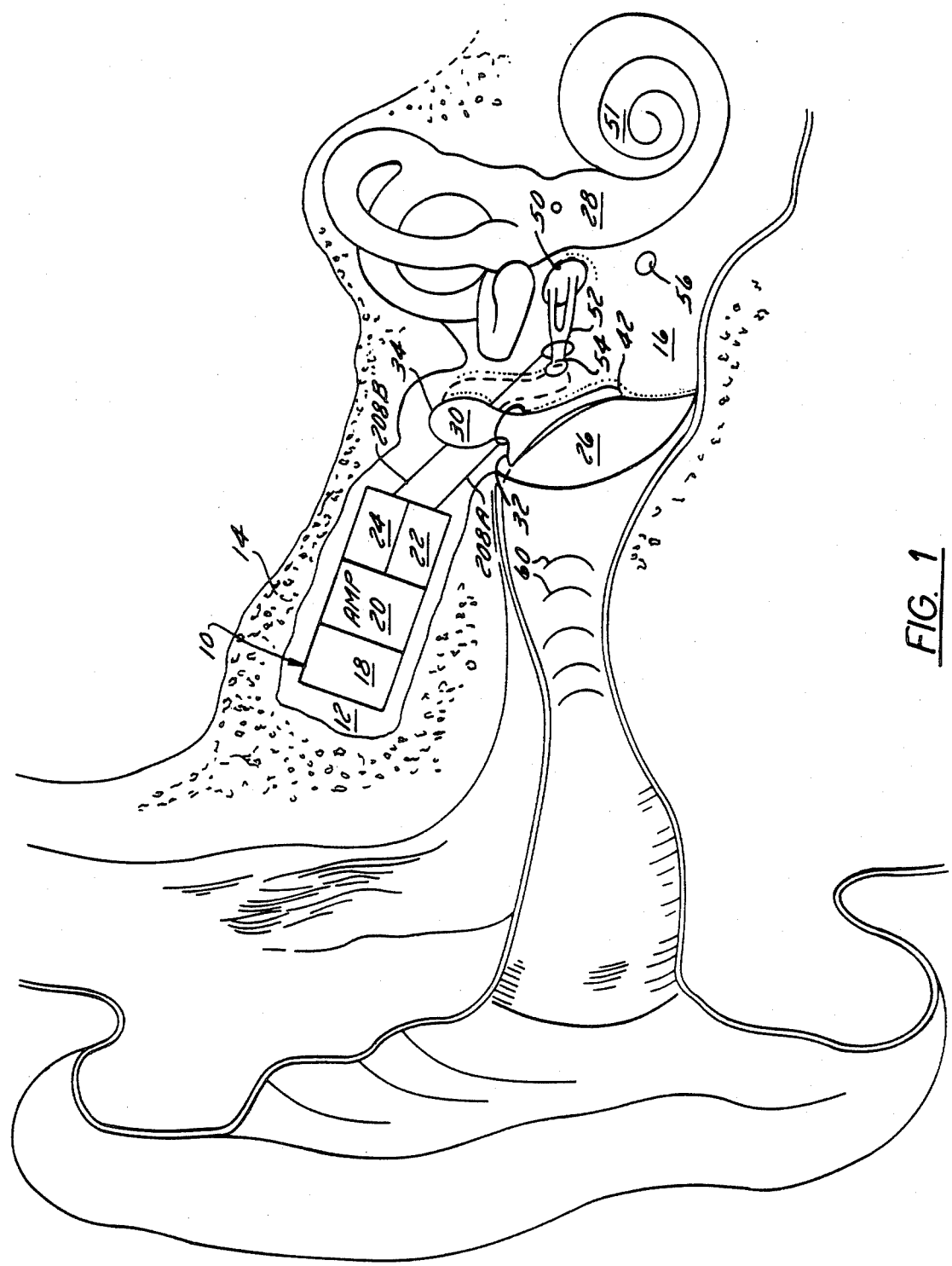
FIG. 1 is a schematic section through a portion of the skull of a human subject adjacent to the ear showing the disposition of one embodiment of an implantable hearing aid in accordance with the present invention.

Referring to FIG. 1, a first embodiment 10 of an implantable hearing device in accordance with the present invention is shown disposed in a surgically developed antrum 12 in the mastoid bone of the subject's skull 14, communicating with the subject's middle ear space 16. Device 10 in this embodiment is comprised of a power source 18, an amplifier 20, a mechanical to electrical input transducer 22 and an electrical to mechanical output transducer 24.

Figure 2:
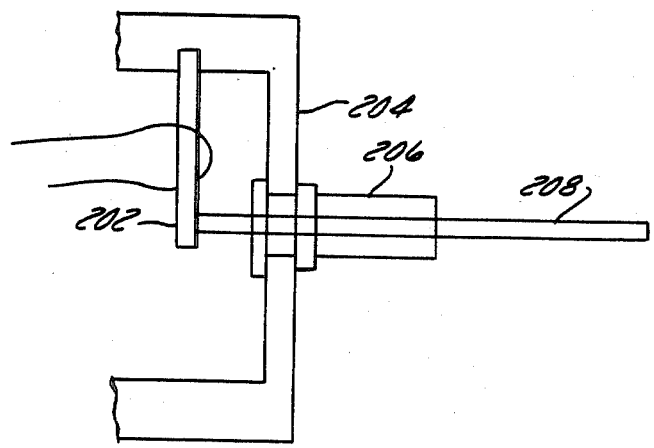
FIGS. 2–5 are schematic illustrations of respective alternative mechanical connections between the transducers and the hearing apparatus of the subject.

Referring briefly to FIG. 2, input transducer 22 and output transducer 24 suitably each comprise a piezoelectric element 202 cooperating with a resilient diaphram 204. A connecting member 208, mounted on and maintained by diaphram 204, is operatively coupled to piezoelectric element 202. Connecting member 208 advantageously is a 0.005 inch diameter stainless steel wire. (The respective wires 208 associated with input transducer 22 and output transducer 24 will be referenced as 208A and 208B, respectively.) A sleeve 206, mounted to housing 204, and slideable retaining wire 208 may be employed to prevent lateral movement and dampen any spurious vibrations.

Input transducer 22 cooperates with tympanic membrane 26 and converts tympanic vibrations corresponding to sound into electrical signals. Input transducer 22, in effect, utilizes tympanic membrane 26 in a manner similar to the diaphram of a microphone. With reference now to FIGS. 1 and 2, the input transducer 22 is mechanically coupled to tympanic membrane 26, suitably by connecting stiff wire 208A to the subject's malleus 30. Connecting wire 208A may be affixed to malleus 30 utilizing surgical techniques similar to those used in ossicular reconstructive surgery, or by other desirable techniques or mechanisms. Examples of connection mechanisms will be described in conjunction with FIGS. 3–5. When sound waves, generally indicated as 60, impinge upon tympanic membrane 26, corresponding tympanic vibrations are initiated. The vibrations are transmitted to malleus 30, and therefrom, through wire 208A to input transducer 22. The mechanical vibrations are converted by piezoelectric element 202 (FIG. 2) to electrical signals. The electrical signals are then applied as input signals to amplifier 20.

The use of the tympanic membrane as an operative portion of the input transducer is particularly advantageous. Permanently percutaneous elements, e.g. wires, ports to the ear canal, etc., typically associated with other input mechanisms such as air-induced microphones, are avoided. Further, the frequency response of the input transducer is in main part determined by the tympanic membrane and other characteristics of the individual subject's hearing mechanism and thus tends to more nearly approximate the frequency response of the subject's normal aural apparatus.

Amplifier 20 operates on the input transducer electrical output signals to generate corresponding amplified input signals to output transducer which are of sufficient magnitude to drive the output transducer element 202, and which compensate for deficiencies in the frequency sensitivity of the subject. Amplifier 20 is typically of the thin film type and suitably comprises any conventional amplifier circuit having input and output electrical impedances in accordance with the electrical impedances of transducers. The frequency response of the amplifier circuit is shaped, as is well known in the art, to compensate for frequency sensitivity deficiencies of the subject. The magnitude of the output signals from amplifier 20 is also limited to a predetermined maximum value to prevent possible injury (acoustic trauma) to the inner ear. The power source 18 for amplifier 20 is preferably a long life lithium-type battery.

Output transducer 24 is utilized to convert the amplified electrical signals representing the tympanic vibrations into mechanical vibrations for application to the inner ear 28 of the subject. The amplified electrical signals are applied as input signals to the piezoelectric element 202 of output transducer 24 and are converted into corresponding mechanical vibrations. The vibrations are communicated to the inner ear by a mechanical connection between wire 208B and the oval window 50 or round window 56, and therethrough to the cochlea 51. The connection between wire 208B and the inner ear can be made in a manner similar to techniques employed in reconstructive surgery using passive mechanical prosthesis devices or by any other suitable mechanism. Exemplary connections will be described in connection with FIGS. 3–5.

As noted above, the mechanical connections between input transducer 22 and tympanic membrane 26 and between output transducer 24 and inner ear 28 are effected utilizing surgical techniques similar to those used in ossicular reconstructive surgery, or by other desired methods. The connections are suitably made by affixing the distal end of stiff wire 208 to an appropriate portion of the ossicular chain, and a portion of the ossicular chain is then utilized as an integral part of the mechanical connection.

Figure 3:
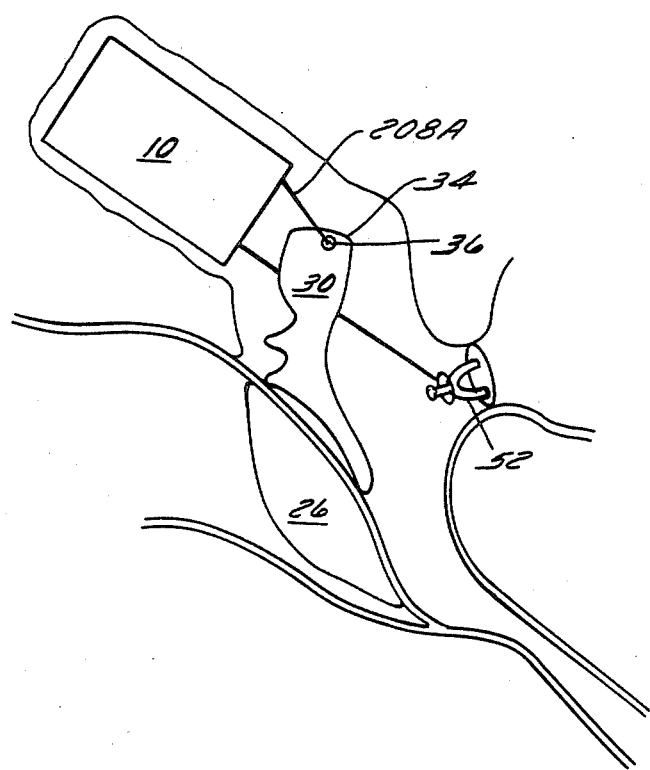
Figure 4:
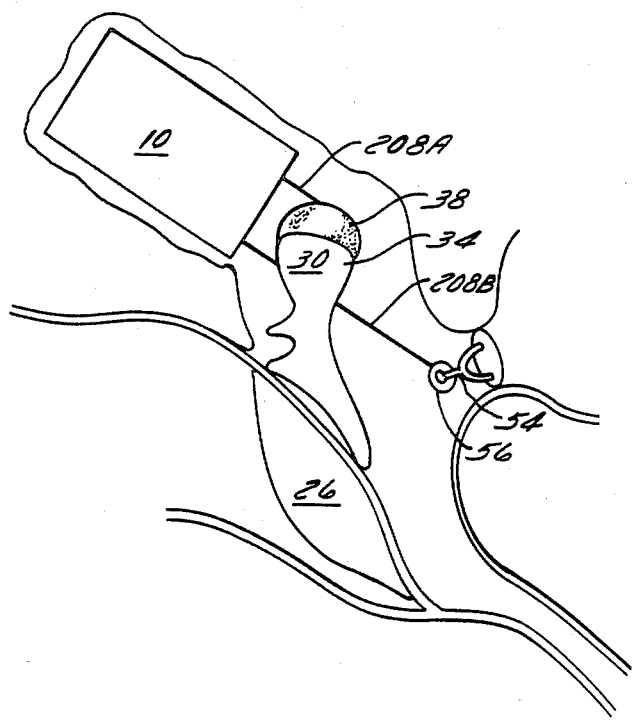
Figure 5:
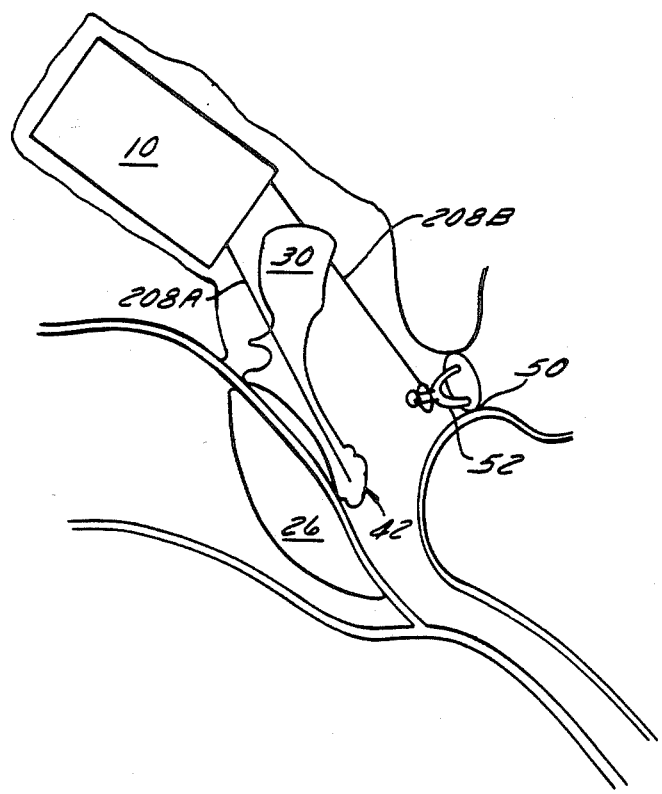

With respect to input transducer 22, the distal end of wire 208A is shown to be affixed to the subject's malleus 30, preferably to the head 34 of malleus 30. For example, as shown in FIG. 3, a small hole 36 may be drilled in the malleus head 34 and the distal end of wire 208A received and secured in hole 36. Wire 208A may be secured by suitable biocompatible cement such as an acrylate ester or fibrin cement. In some instances, wire 208A may be fixed to malleus head 34 solely through use of a biocompatible cement without the necessity of hole 36. Alternatively, as schematically shown in FIG. 4, the coupling to malleus 30 can be effected through use of an intermediary fitting (cap) 38, articulating with malleus head 34. It may, however, be desirable in some circumstances to affix wire 208A to portions of the malleus 30 other than head 34. For example, as shown in the embodiment of FIG. 1, the distal end of wire 208A may be looped about the neck 32 of malleus 30. Alternatively, wire 208A may be coupled to the tip of the manubrium 42 of malleus 30. Such a connection is schematically shown in FIG. 5. The attachment is preferably effected utilizing biocompatible cement as noted above, or by drilling a hole in manubrium 42 for receiving the distal end of wire 208A.

With respect to output transducer 24, the distal end of wire 208B is suitably affixed to the subject's stapes 52. As schematically shown in FIG. 1, the distal end of wire 208B may be looped about the capitulum 54 of stapes 52, or, as schematically shown in FIG. 4, an intermediate fitting 56 articulating with capitulum 54 may be employed. Likewise, the connection can be effected utilizing biocompatible cement. In some instances, it may be desirable to effect a connection between 208B and the crus or footplate portions of the stapes or directly to the oval window in accordance with well known reconstructive surgical techniques.

It may, however, be desirable in some circumstances, to effect a connection between wire 208B and the round window 56 rather than to the oval window. A direct connection to the round window input to the cochlea may be effected utilizing a device fashioned from biocompatible materials simulating a footplate disposed over the round window membrane, to which wire 208B is attached.

Figure 6:
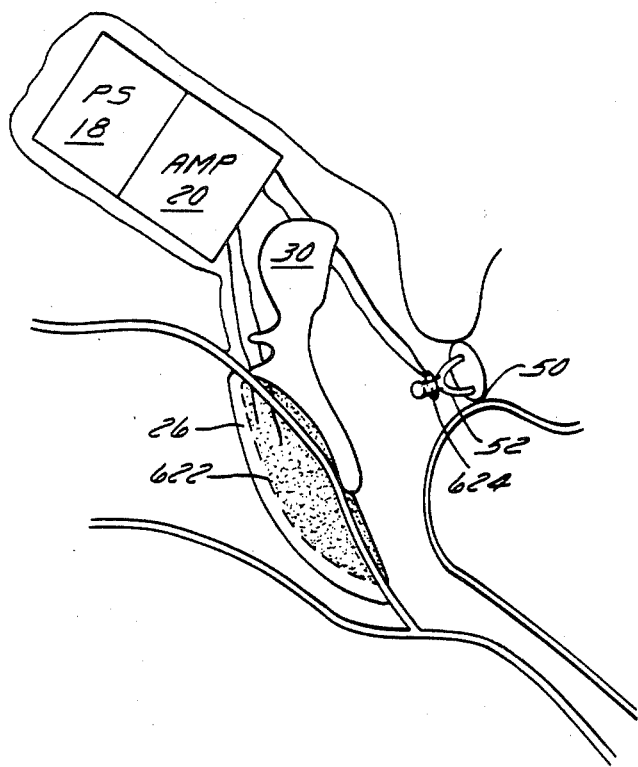
FIG. 6 is a schematic illustration of a further embodiment of the present invention utilizing polymeric piezoelectric film transducers.

In accordance with another embodiment of the present invention, one or both of input transducer 22 and output transducer 24 can be formed from a polymeric piezoelectric film such as polyvinylidene fluouride (PVDF) disposed directly on an appropriate element of the subject's physical hearing apparatus and electrically connected to amplifier 20. One such embodiment of the present invention is illustrated in FIG. 6, wherein respective PVDF films 622 and 624 are utilized as the input and output transducers, respectively. Input transducer PVDF film 622 is disposed on the inner surface of tympanic membrane 26, underlying the manubrium 42 of malleus 30. Alternatively, PVDF film 622 could be disposed on malleus 30, preferably on the underside of the manubrium or otherwise interposed between the tympanic membrane 26 and the underside of the manubrium of malleus 30. Film 622 is electrically connected to the input terminals of amplifier 20.

Input transducer PVDF film 624 is disposed on stapes 52, or directly on oval window 50 or round window 56, and is electrically connected to the output terminals of amplifier 20. When soundwaves impinge on tympanic membrane 26 and generate tympanic vibrations, such vibrations are sensed by film 622 and converted into electrical signals for application to amplifier 20. The amplified electrical signals are then applied to output transducer film 624 which converts the amplified signals into mechanical vibrations for transmission to the inner ear.

The ossicular chain is broken in implementing the present invention to prevent positive feedback of the amplified vibrations to the input transducers from occurring. The break would typically be effected by removing at least one of the component parts of the ossicular chain, typically the incus. It is desirable to maintain the malleus and stapes in normal anatonomical position with muscle and tendon intact to maintain the subject's natural defense mechanism against acoustic trauma.

Figure 7:
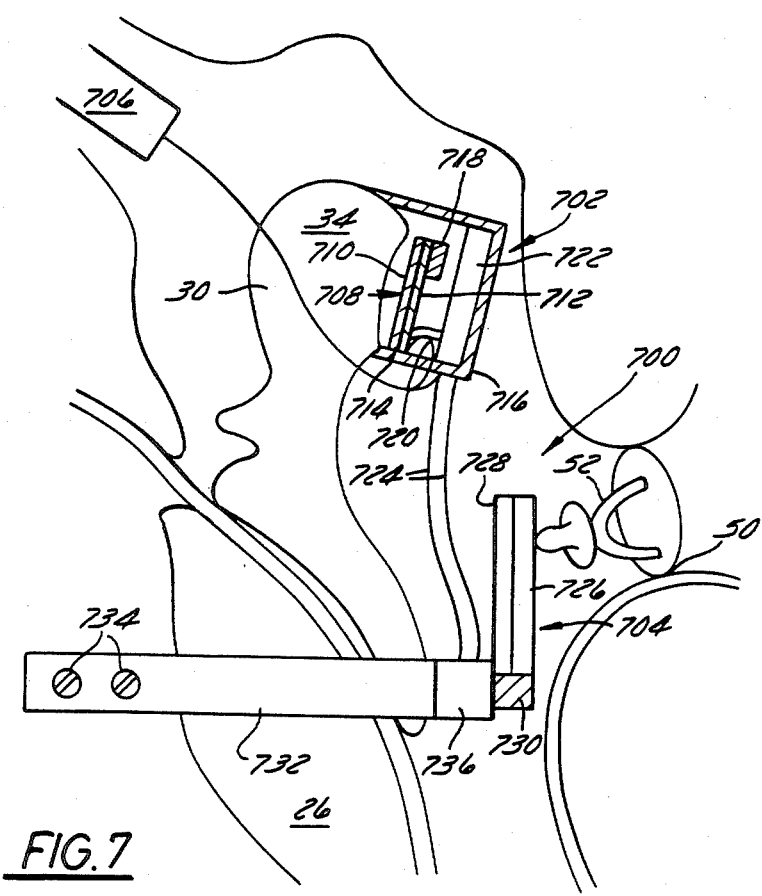
FIG. 7 is a schematic illustration, partly in section, of a preferred alternate embodiment, showing a transducer in an accelerometer configuration.

FIG. 7 illustrates an alternate and highly preferred embodiment of an implantable hearing aid 700 in accordance with the present invention. The hearing aid 700 is comprised of paired transducer means for mediating electrical/mechanical signals, in this instance a first or input transducer means designated generally as 702 and a second or output transducer means designated generally as 704. The transducers are powered by a power supply 706 disposed within an antrum formed in the bony structure proximate the ear of the subject receiving the implant. The input transducer 702 is operatively associated with the head 34 of the maleus 30 which vibrates in response to movement of the eardrum as acoustical energy impinges upon it. The transducer 702 in this embodiment is shown to be in the configuration of a piezoelectric accelerometer, comprised of a piezoelectric bimorph 708 having a first piezoelectric crystal element 710 lying in generally face-to-face relationship with an opposed crystal 712. The bimorph 708 is cantilevered at its first end 714 from an enveloping structure or implanting shield 716, the terminal edges of which are secured to the head 34 of malleus 30 by means of a suitable biocompatible adhesive or other surgically acceptable means. The accelerometer configuration is achieved in this embodiment by a structural weight 718 secured to one of the crystals such as crystal 712 at the end opposite that cantilevered from the implanting shield 716. In this configuration, when the malleus vibrates coincident with tympanic vibrations the weight 718 imparts an inertial response to the bimorph 708 which will itself then vibrate in a mechanical pattern replicating the vibration of the malleus. Recognizing that the forces extant the tympanic membrane have been determined to be extraordinarily intense, beyond that previously appreciated, the accelerometer configuration offers enhanced efficiency. Then too, since the bimorph 708 is cantilevered or otherwise anchored directly from the mounting structure, the problems inherent in the placement of these types of elements within a mucous membrance environment are greatly alleviated.

Vibrations in the accelerometer are converted to electrical signals as a consequence of the inherent characteristics of piezoelectric crystals. These electric signals are applied via signal leads 720 to an amplifier 722. Depending upon the characteristics of the amplifier 722, a suitable or sufficient gain may be realized allowing those electric signals to be applied directly to the output or second transducer 704; otherwise the amplifier 722 may be used as a preamp and a separate amplifier associated with the transducer 704 will be provided. Regardless, the signals from amplifier 722 are routed through the middle ear space via signal lines 724 for ultimate application to the output transducer. In this context, the signal leads along with the associated amplifier circuitry thus constitute transmission means for communicating between the input and output transducers in lieu of communication through the ossicular chain.

The output transducer of this embodiment is a bimorph piezoelectric crystal structure comprised of a pair of piezo electric crystals 726 and 728 cantilevered at a first end from a support element 730. The support element 730 is mounted on an arm 732 secured to a bony region of the subject by means of fixture elements 734, such as surgical screws. This fixturing approach is conceived to be most reliable physically and functionally due to the difficulty of implanting devices in the mucous membrane environment of the middle ear. The mounting member 732 thus places the output transducer 704 in proximate contact with the stapes 52 whereby vibrations in the output transducer 704 are communicatively coupled thereto. Depending upon the electrical characteristics of the amplifier 722 as noted above, an optional amplifier 736 may be provided for driving the output transducer 704. These are matters, however, which can be tailored at the time the device and its associated circuitry are designed.

As is evident from the description of the structure in FIG. 7, it can be seen that the transducers 702 and 704 are surgically interposed within the ossicular chain in replacement, in this instance, of the incus. The transducers and associated circuitry bridge the interruption in the ossicular chain resultant from removal of the incus to form an independent link between the tympanic membrane and the inner ear. In this fashion the potential for mechanical feedback is entirely eliminated, resulting in both improved efficiencies and comfort to the subject. And, when it is the incus which is removed in order to interrupt the ossicular chain and prevent transmission of mechanical vibrations, the skeletomuscular network of the subject maintains the natural defense mechanism against acoustic trama should excessively loud noises be encountered.

It will be understood that the above description is of preferred exemplary embodiments of the present invention and that the invention is not limited to the specific forms shown. For example, it is not necessary that each of the components in the embodiment of FIG. 1 be disposed in a unitary housing. Rather, the various components can be physically separated. Further, the respective components may in some instances be disposed in the natural middle ear space of the subject, rather than in a surgically developed antrum. These and other modifications may be made in the design and arrangement of the components without departing from the spirit of the invention as expressed in the appended claims.

What is claimed:

1. A method for improving the hearing of a hearing-impaired subject, said subject, if anatomically normal, having a tympanic membrane intended for generating mechanical tympanic vibration in response to sound waves impinging thereon, an inner ear responsive to mechanical vibrations, and an ossicular chain intended for communicating mechanical vibrations from said tympanic membrane to said inner ear, said method comprising the steps of:

interrupting the ossicular chain to preclude transmission of mechanical vibrations between the tympanic membrane and inner ear of a subject; and, surgically interposing an implant comprising input and output transducer means for mediating mechanical/electrical signals, having controlled amplification characteristics, within the interrupted ossicular chain to bridge the interruption therein and form an independent link between said tympanic membrane and said inner ear;

wherein said transducer means includes first transducer means operatively associated with said tympanic membrane for receiving mechanical tympanic vibrations therefrom and converting the same into electrical signals characteristic thereof, second transducer means operatively associated with said inner ear for receiving amplified electrical signals and converting the same into mechanical vibrations replicating said tympanic vibrations and transmission means for communicating between said first and second transducer means in lieu of said ossicular chain.

2. The method of claim 1, wherein said interrupting step comprises removing at least one of the component parts from said ossicular chain.

3. The method of claim 2, wherein said interrupting step comprises removing the incus from the ossicular chain.

4. The method of claim 1, wherein said step of surgically interposing said implant comprises disposing a mechanical to electrical transducer in operative communication with said tympanic membrane.

5. The method of claim 1, wherein said step of surgically interposing said implant comprises effecting an operative mechanical connection between said tympanic membrane and a piezoelectric transducer.

6. The method of claim 1 wherein said step of surgically interposing said implant comprises disposing a mechanical to electrical input transducer for communication with the middle ear space of said subject; and effecting a mechanical connection between an element of the ossicular chain and said input transducer.

7. The method of claim 6, wherein said disposing step comprises disposing said input transducer within the middle ear space of said subject.

8. The method of claim 6, wherein said step of effecting a mechanical connection comprises:

looping a first end of a stiff connecting member about the neck of the malleus between the manubrium and the head of said malleus, and mechanically linking the other end of said connecting member to said input transducer.

9. The method of claim 6, wherein said step of effecting a mechanical connection comprises:

drilling a hole in the head of the malleus;

inserting a first end of a stiff connecting member in said hole; and mechanically linking the other end of said connecting member to said input transducer.

10. The method of claim 6, wherein said step of effecting a mechanical connection comprises:

disposing a fitting on the head of said malleus, such that said fitting articulates with said malleus;

mechanically coupling a first end of a stiff connecting member to said fitting, whereby said connecting member moves in accordance with movement of said malleus; and mechanically linking the other end of said connecting member to said input transducer.

11. The method of claim 6, wherein said step of effecting a mechanical connection comprises fixing a first end of a stiff connecting member to said malleus by means of biocompatible adhesive material.

12. The method of claim 11, wherein said fixing step comprises fixing said first end of said connecting member by means of an acrylate ester cement.

13. The method of claim 11, wherein said fixing step comprises fixing said first end of said connecting member by means of a fibrin cement.

14. The method of claim 6, wherein said step of effecting mechanical connection comprises:

coupling a first end of a stiff connecting member to the malleus in the vicinity of the tip of the manubrium; or mechanically linking the other end of said connecting member to said input transducer.

15. The method of claim 1, wherein said step of surgically interposing said implant comprises disposing a mechanical to electrical transducer on the malleus of said ossicular chain.

16. The method of claim 1, wherein said step of surgically interposing said implant comprises disposing a polymeric mechanical to electrical transducer film in operative association with said tympanic membrane.

17. The method of claim 16, wherein said film is a polyvinylidene flouride (PVDF) flim.

18. The method of claim 17, wherein said step of surgically interposing said implant comprises communicating electrical signals generated by said film to an electrical to mechanical output transducer.

19. The method of claim 16, wherein said step of surgically interposing said implant comprises effecting a communicative electrical connection between said transducer film and an electrical to mechanical output transducer.

20. The method of claim 16, wherein said step of surgically interposing said implant comprises disposing a polyvinylidene fluoride (PVDF) film on the malleus of said ossicular chain.

21. The method of claim 1, wherein said step of surgically interposing said implant comprises disposing a polymeric mechanical to electrical transducer film on the malleus of said ossicular chain.

22. The method of claim 21 wherein said step of surgically interposing said implant comprises effecting a communicative electrical connection between said transducer film and an electrical to mechanical output transducer.

23. The method of claim 1, wherein said step of surgically interposing said implant comprises surgically implanting at least one piezoelectric film transducer in the middle ear of said subject.

24. The method of claim 1, wherein said step of surgically interposing said implant comprises surgically implanting at least one piezoelectric crystal force transducer in the middle ear of said subject.

25. The method of claim 1, wherein said step of surgically interposing said implant comprises surgically implanting at least one piezoelectric accelerometer in the middle ear of said subject.

26. The method of claim 1, wherein said step of surgically interposing said implant comprises surgically implanting at least one electromagnetic transducer in the middle ear of said subject.

27. An implantable apparatus for improving the hearing of a hearing impaired subject, said subject having a hearing apparatus which, if anatomically normal, comprises a tympanic membrane intended for generating mechanical tympanic vibrations in response to sound waves impinging thereon, and an ossicular chain intended to communicate said tympanic vibrations to the inner ear of said subject, said apparatus comprising
input and output transducer means for mediating mechanical/ electrical signals having controlled amplification characteristics, configured for bridging disposition in an interrupted ossicular chain of a subject as an electromechanically independent link between the tympanic membrane and inner ear of said subject, comprised of first transducer means for operative association with said tympanic membrane for receiving mechanical tympanic vibrations therefrom and converting the same into electrical signals characteristic thereof, second transducer means for operative association with said inner ear for receiving said electrical signals and converting the same into mechanical vibrations replicating said tympanic vibrations and transmission means for communicating between said first and second transducer means in lieu of said ossicular chain or portion thereof.

28. The apparatus of claim 27, wherein said first transducer means is adapted for disposition in communication with the middle ear space of said subject, said apparatus further comprising
means for effecting a mechanical connection between said tympanic membrane and said first transducer.

29. The apparatus of claim 28, wherein said ossicular chain is broken medial to the malleus of said ossicular chain and said means for effecting a mechanical connection comprises
a stiff connecting member having a first end thereof mechanically linked to said first transducer; and
means for coupling said connecting member to said malleus such that said connecting member moves in accordance with movement of said malleus.

30. The apparatus of claim 29, wherein said means for coupling comprises a fitting adapted to receive the head of said malleus such that said fitting articulates with said malleus, said apparatus further comprising
means for mechanically coupling said connection member to said fitting.

31. The apparatus of claim 29, wherein said means for coupling comprises a loop formed in the end of said connecting member adapted to at least partially circumscribe the neck of said malleus between the manubrium and the head of said malleus.

32. The apparatus of claim 31, wherein said transmission means comprises:
an amplifier, receptive as input signals of said first transducer electrical output signals, and electrically coupled to said second transducer means.

33. The apparatus of claim 32, wherein said second transducer means comprises a polymeric electrical to mechanical transducer film, disposed in mechanical connection with said inner ear, and receptive of, as input signals thereto, said first transducer means electrical output signals.

34. The apparatus of claim 33, wherein said second transducer polymeric film is disposed on the stapes of said ossicular chain.

35. The apparatus of claim 33, wherein said second transducer polymeric film is disposed on the oval window membrane.

36. The apparatus of claim 33, wherein said second transducer polymeric film is disposed on the round window membrane.

37. The apparatus of claim 28, wherein said means for mechanically coupling comprises a fitting adapted to receive the subject's stapes capitulum such that said stapes articulates with said fitting, said apparatus further comprising means for linking said output connecting member to said fitting.

38. The apparatus of claim 27, wherein said first transducer means comprises:
a polymeric mechanical to electrical transducer film disposed on said tympanic membrane, said apparatus further comprising
means for communicating electrical output signals generated by said input transducer film to said output transducer.

39. The apparatus of claim 38, wherein said first transducer means polymeric film comprises polyvinylidene fluoride.

40. The apparatus of claim 39, wherein said second transducer means comprises a polymeric electrical to mechanical transducer film, disposed in mechanical connection with said inner ear, and receptive of, as input signals thereto, said first transducer means electrical output signals.

41. The apparatus of claim 38, wherein said second transducer means comprises:
a polymeric electrical to mechanical transducer film, disposed in mechanical connection with said inner ear, and receptive of, as input signals thereto, said first transducer means electrical output signals.

42. The apparatus of claim 41, wherein said second transducer polymeric film is disposed on the stapes of said ossicular chain.

43. The apparatus of claim 38, wherein said second transducer means comprises a polymeric electrical to mechanical transducer film, disposed in mechanical connection with said inner ear, and receptive of, as input signals thereto, said first transducer means electrical output signals.

44. The apparatus of claim 27, wherein said second transducer means comprises:
an electrical to mechanical output transducer adapted for disposition in communication with the middle ear space of said subject, said apparatus further comprising
means for transmitting mechanical vibrations from said second transducer to said inner ear.

45. The apparatus of claim 44, wherein said transmission means comprises:
a stiff output connecting member, coupled at a first end thereof to said second transducer; and means for mchanically coupling said connecting member to said inner ear.

46. The apparatus of claim 45, wherein said means for mechanically coupling comprises a fitting adapted to receive the subject's stapes capitulum such that said stapes articulates with said fitting, said apparatus further comprising means for linking said output connecting member to said fitting.

47. The apparatus of claim 44, wherein said means for mechanically coupling comprises means for coupling said output connecting member to the stapes of said ossicular chain.

48. The apparatus of claim 27, wherein at least one of said transducer means is a piezoelectric film transducer.

49. The apparatus of claim 27, wherein at least one of said transducer means is a piezoelectric crystal force transducer.

50. The apparatus of claim 27, wherein at least one of said transducer means is a piezoelectric accelerometer.

51. The apparatus of claim 27, wherein at least one of said transducer means is an electromagnetic transducer.

52. In an apparatus of the type including means for generating electrical signals indicative of soundwaves impinging on the ears of said subject and means, responsive to said electrical signals, for generating mechanical vibrations for transmission to the inner ear of said subject, the improvement wherein said means for generating electrical signals comprises a mechanical to electrical transducer connected to the malleus of said subject such that said transducer is mechanically driven by said malleus and is responsive to vibrations effected by sound waves impinging on the tympanic membrane of the subject.

* * * * *